(12) United States Patent
Campos et al.

(10) Patent No.: US 12,268,385 B2
(45) Date of Patent: Apr. 8, 2025

(54) SURGICAL STAPLE

(71) Applicant: Taurus Endoscopy SAS, Strasbourg (FR)

(72) Inventors: Guillaume Campos, Strasbourg (FR); Mariel Elizabeth Bolhouse, Redwood City, CA (US); Bruno Mutet, La Wantzenau (FR)

(73) Assignee: Taurus Endoscopy SAS, Strasbourg (FR)

( * ) Notice: Subject to any disclaimer, the term of this patent is extended or adjusted under 35 U.S.C. 154(b) by 0 days.

(21) Appl. No.: 18/660,645

(22) Filed: May 10, 2024

(65) Prior Publication Data

US 2024/0374254 A1 Nov. 14, 2024

Related U.S. Application Data

(60) Provisional application No. 63/465,560, filed on May 11, 2023.

(51) Int. Cl.
*A61B 17/064* (2006.01)
*A61B 17/00* (2006.01)
*A61B 90/00* (2016.01)

(52) U.S. Cl.
CPC .. *A61B 17/064* (2013.01); *A61B 2017/00296* (2013.01); *A61B 2017/0645* (2013.01); *A61B 2090/035* (2016.02)

(58) Field of Classification Search
CPC .............. A61B 17/064; A61B 17/0644; A61B 17/0684; A61B 17/122; A61B 17/128; A61B 17/1285; A61B 2017/00234; A61B 2017/00296; A61B 2017/0645; A61B 2017/1225; A61B 2090/035
See application file for complete search history.

(56) References Cited

U.S. PATENT DOCUMENTS

| | | | |
|---|---|---|---|
| 5,470,010 A | 11/1995 | Rothfuss et al. | |
| 11,547,419 B2 | 1/2023 | Alzaga et al. | |
| 2004/0028502 A1* | 2/2004 | Cummins | A61B 17/0644 411/457 |
| 2005/0267530 A1 | 12/2005 | Cummins | |
| 2008/0173693 A1 | 7/2008 | Mas et al. | |
| 2008/0177300 A1* | 7/2008 | Mas | A61B 17/0057 606/151 |
| 2008/0269803 A1 | 10/2008 | Sater | |
| 2009/0093826 A1 | 4/2009 | Warder-Gabaldon | |
| 2009/0272786 A1 | 11/2009 | Zeiner et al. | |

(Continued)

OTHER PUBLICATIONS

European Patent Office, Extended Search Report Communication in EPO Application No. 24315232.9 (Aug. 29, 2024).

*Primary Examiner* — Robert A Lynch
(74) *Attorney, Agent, or Firm* — Harness, Dickey & Pierce, PLC

(57) ABSTRACT

A surgical staple includes multiple arms extending from a transverse connection area, each of the arms having tissue-gripping teeth and a resistance area of increased width located between the transverse connection area and the gripping area. In another aspect, a surgical staple includes two arms connected by an arcuate folding joint, with a deformation area located between the folding joint and a laterally enlarged resistance area, and with laterally projecting teeth longitudinally located outboard of the resistance area on each of the arms.

20 Claims, 6 Drawing Sheets

(56) References Cited

U.S. PATENT DOCUMENTS

| | | | |
|---|---|---|---|
| 2011/0144691 A1* | 6/2011 | Cummins | A61B 17/0644 |
| | | | 606/219 |
| 2017/0020517 A1 | 1/2017 | Coleman et al. | |
| 2017/0202552 A1 | 7/2017 | Coleman et al. | |
| 2018/0000482 A1 | 1/2018 | Alzaga et al. | |
| 2018/0028181 A1* | 2/2018 | Alzaga | A61B 17/00234 |
| 2021/0128154 A1* | 5/2021 | Alzaga | A61B 17/122 |

* cited by examiner

SURGICAL STAPLE

CROSS-REFERENCE TO RELATED APPLICATION

This application claims priority to U.S. provisional patent application Ser. No. 63/465,560, filed on May 11, 2023, which is incorporated by reference herein.

BACKGROUND AND SUMMARY

The invention relates to the field of medical devices and more specifically to closure and hemostasis systems for surgical interventions. The staple can be used for closure of tissue incisions, control bleedings or to anchor devices within a hollow organ.

Multiple staples have been proposed in the past. Some of those proposed are based on a staple made of a single metal piece deformed using an applier into a shape which anchors the staple on tissue. Such staples include U.S. patent publication n° 2018/0028181, which is incorporated by reference herein. Conventional staples are very sensitive to unpredictable external forces which interfere with the staple deformation process.

In accordance with the present invention, a surgical staple includes multiple arms extending from a transverse connection area, each of the arms having tissue-gripping teeth and a resistance area of increased width located between the transverse connection area and the gripping area. In another aspect, a surgical staple includes two arms connected by an arcuate folding joint, with a deformation area located between the folding joint and a laterally enlarged resistance area, and with laterally projecting teeth longitudinally located outboard of the resistance area on each of the arms. A further aspect of a surgical staple includes an endoscope and a staple configured to fold and grip tissue folds, with the staple including a thin deformation area, a wider resistance area and at least one gripping tooth on each of multiple arms. A method of using a surgical staple is also provided.

The present staple overcomes drawbacks of conventional devices by proposing a staple that is designed to withstand external forces and improve the reliability of the deformation of the staple by an applier. The present staple relates to a surgical staple comprising 2 arms emerging from a transverse connection area, each of said arms having a gripping area and an attachment end wherein each of said 2 arms further comprise a resistance area located between the transverse connection area and the gripping area.

The staple is intended to be deformed through interaction with an applier which results in a folding of the staple where each arm approaches the other. The direction in which the tip of the arms move upon folding, is referred to herein as the "forward direction," And the opposite direction will be referred to as the "back direction."

In a preferred embodiment, the staple is intended to be deformed by being pulled in the back direction within a hollow tube acting as an anvil. At least one deformation area, connecting between resistance areas, is deformed during deformation of the staple into the closed shape. In another preferred embodiment, the staple is pulled in the back direction against an anvil element which will have at least one contact point with the deformation area of each arm. The anvil can be for example a hollow tube or any hollow shape allowing contact points with the deformation area of each arm. At least the deformation area is deformed during the folding of the staple.

In one embodiment the staple has a constant thickness and is cut from a single sheet of metal such as titanium. This embodiment offers the benefit of being produced with a simple and straight forward process. In another embodiment the staple has a variating thickness. In particular, it has a superior thickness in the resistance area compared to other areas of the staple. Additional advantages and features of the present staple will become apparent from the following description and claims, and appended figures.

DETAILED DESCRIPTION

In general, a staple includes a transverse connection area from which 2 arms emerge. Each arm extends with first a deformation area. This deformation area is in contact with a tip of an applier during deformation of the staple. In a preferred embodiment the deformation area is curved towards a back direction (see FIG. 3). The deformation area has a width that is adapted depending on the application. The force necessary to deform the staple into closed position is dependent on the volume and shape of the metal composing the deformation area. The force necessary also depends on the legs of the arms.

In certain applications, such as flexible endoscopy, the force that can be transferred to the staple is limited by the equipment. It is thus desirable for this application to maintain the volume of metal of the deformation small compared to other areas of the staple.

Figure 3:
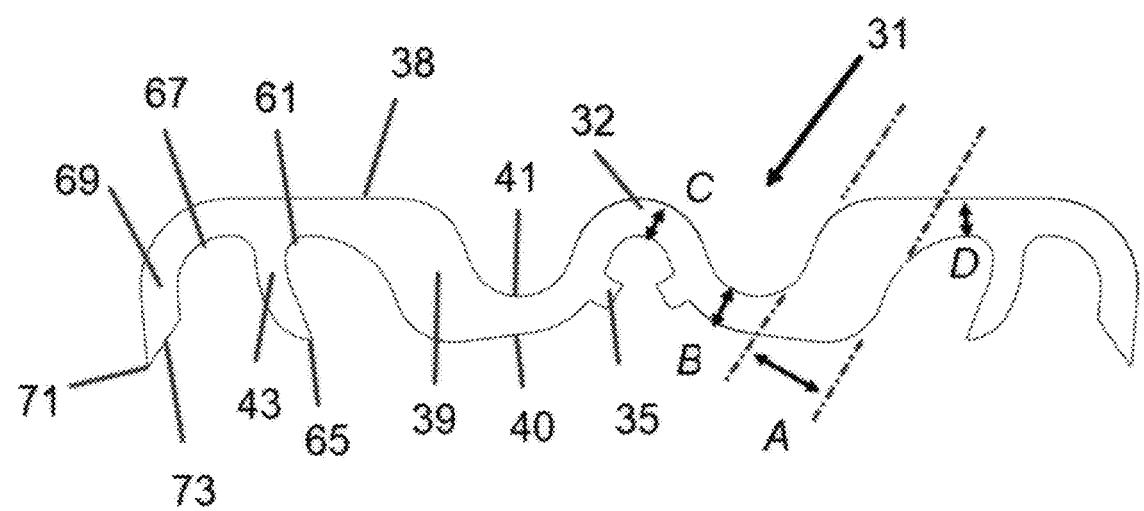
FIG. 3 is an elevational view showing the first embodiment of the present surgical staple.

In a certain embodiment, such as the one depicted in FIG. 3, the staple has a constant thickness and the width of the deformation area is substantially smaller than the width of the resistance area. The width is being measured in the plane of the paper sheet.

Especially in minimally invasive intervention applications, the necessary force for deformation and application must be kept low. It is therefore undesirable to increase the material volume of the whole staple (thickness or width) to rigidify it since this would result in an application force incompatible with the regular equipment used in minimally invasive interventions.

On the forward size, the deformation area of each arm becomes flat after the curve. This flat section will be continued in the resistance area to create a long flat portion on the forward side. A flat in front helps limit the closure and provides a high resistance "positive stop" for the deformation which triggers the opening of the deformable connection.

In a preferred embodiment, the back side of the deformation area, as can be seen on FIG. 3, has a curved shape. This curve shape allows the staple to rest on contact points of the anvil when the staple is pulled in the back direction. It is of interest that the staple could be held firmly against the tip of the applier during medical procedures.

During the staple folding, the staple will slide in the back direction with respect to the anvil of the applier and the contact point between the anvil and the staple will progressively move towards the extremity of the arms of the staple. The curve shape on the back side of the deformation area allows that as the staple folds and as the staples slides towards the anvil, the surface of the staple in contact with the anvil is at an angle closer to 90° with the surface of the anvil, therefore maximizing the lever effect and hence the efficiency of the staple closure.

The staple is intended to be deformed and delivered on tissue by means of a dedicated applier. Once delivered, the staple applies pressure on the tissue trapped between the staple arms. The clinical impact desired may include tissue closure, hemostasis, stent or tube anchoring or marking of lesions.

To create a lasting clinical action the staple needs to apply a compression force to the tissue trapped between the arms and should resist the natural movement of the gastrointestinal (GI) tract as well as resisting the passage of the GI content. The staple thus needs to hold strongly on the tissue on which it is attach. A strong anchoring on tissue happens when the staple closes symmetrically: that is when the staple arms exactly face each other across the tissue.

The staple should also not cut through tissue when deformed on the tissue. Tissue cutting may happen when the clip arms are deformed so that the arms cross: that is when the tip of one of the arm moves beyond the opposite arm.

Before being deformed on tissue the clinician using the invention often needs to interact with the tissue by means of the staple. Often the intended goal is to displace tissue for example to approximate the edges of a wound or an opening to be closed. The forces applied by the user on the tissue may be close to the force needed to deform the clip. It is desirable that the clip be resistant to those action and that, as a result, the clip could still be fired and have a nice behavior after some tissue manipulation has occurred.

When the staple is closed in clinical practice both the interaction with the dedicated staple applier and the interaction with the tissue on which the staple will be applied, create forces and small displacements of the staple which significantly impact the staple closure. The staple is expected to close by folding as follows: during closure, one arm approaches the other until the gripping areas and attachment ends get very close to one another with tissue trapped in between.

The staple application includes in particular tissue manipulation especially to approximate the edges of an incision to close. During this manipulation, different forces are applied on the arms of the staple. These forces may be applied in different directions. Application of these undesired and unpredictable forces may result in faulty closure. Those faulty closures may be of different natures:

The staple may be bent in the back direction towards the applier before the closure deformation is initiated.

The staple may close out of the plane, one arm missing each other.

These undesired events result in poor application of the staple which in turn result in poor medical outcomes: the staple may not compress the tissue at all or compress it less than it would have, should the staple have been closed properly.

To prevent these issues, the staple proposed herewith comprises a resistance area located on each arm between the deformation area and the gripping area. The purpose of this resistance area is to prevent deformation of the staple in the back direction before closure deformation is initiated and also to prevent asymmetric deformation of the arms out of the closure plane.

It is desired to keep the deformation force of the staple low. The resistance area comprises more metal material than the deformation area. Moreover, the resistance area extends in the back direction (where space is available). The resistance area is contained within the "staple thickness" to allow minimally invasive placement.

In particular, in one embodiment with a staple of constant thickness shown in FIG. 3, the resistance area has a mean width superior to the deformation area. The width of the resistance area is variating since it has a progressive shape linking the deformation area to the arms extension from which the gripping area and attachment end emerge. In a preferred embodiment, the resistance area has a maximum width that is at least the double of the width of the transverse connection area.

Extending the staple within the plane that contains the staple increase the resistance in the direction normal to that plane which is, from pre-clinical experience the major issue. Compared to increasing the staple thickness locally it maximizes the efficiency of resistance per volume of matter added. Also, maintaining a staple shape that can be cut from a sheet of metal is efficient in terms of manufacturing costs.

The staple acts by trapping tissue between the arms. In the closure and hemostasis embodiments, the tissue is more specifically trapped between the teeth emerging from arms. It is thus not possible to increase the width of the staple arms in the griping area. As a result, introducing a resistance area with an increased thickness compared to the arms section where tissue is trapped is beneficial to the staple performance.

In another preferred embodiment the resistance area has a width that is at least double of the width of the arm segment connecting the gripping area with the attachment end. In another embodiment, the resistance area may have a thickness increased compared to the deformation area and or other sections of each arm. In yet another embodiment, represented in FIG. 3, each arm of the staple comprises a resistance area that has both a width and a thickness superior to the deformation area. The increased width of the resistance area compared to the deformation area allows for a more reliable staple deformation while maintaining the application force low.

Another issue happening during real life staple closure is the phenomenon called "overclosure" where the arms of the staple are deformed too far and end up crossing each other. This also results in bad performance of the staple and potentially adverse events since the staple may cut through tissue.

To avoid this phenomenon, in one embodiment, the resistance area comprises flat zones on the forward side as seen on FIG. 3. For avoidance of a doubt this flat zone is located, for each arm, on the same edge than the edge from which the gripping area emerges. Upon closure, the flat zone of the resistance areas of each arms progressively contact each other and contact each along all their length when the staple is fully closed. These flat shape efficiently avoids overclosure even in the case of slight misalignment between the staple and the applier.

Since the 2 flat zones of the resistance areas progressively contact each other, this results in the fulcrum point progressively moving along the flat zone which results in a more efficient force transfer from the applier to the arm tips. The introduction of a flat zone on the forward side of the resistance area results in both the prevention of undesirable event that hard to control otherwise but also in the reduction of the necessary closure force which is an important limitation of the minimally invasive modalities.

Another challenge of minimally invasive modalities is the geometric constraints that the instrument needs to comply with. The flat zone on the forward side of the resistance area is compatible with those constraints and improves advancement of the staple through different sheath and/or tubes necessary for reaching the site of application with minimally invasive modalities.

Figure 1:
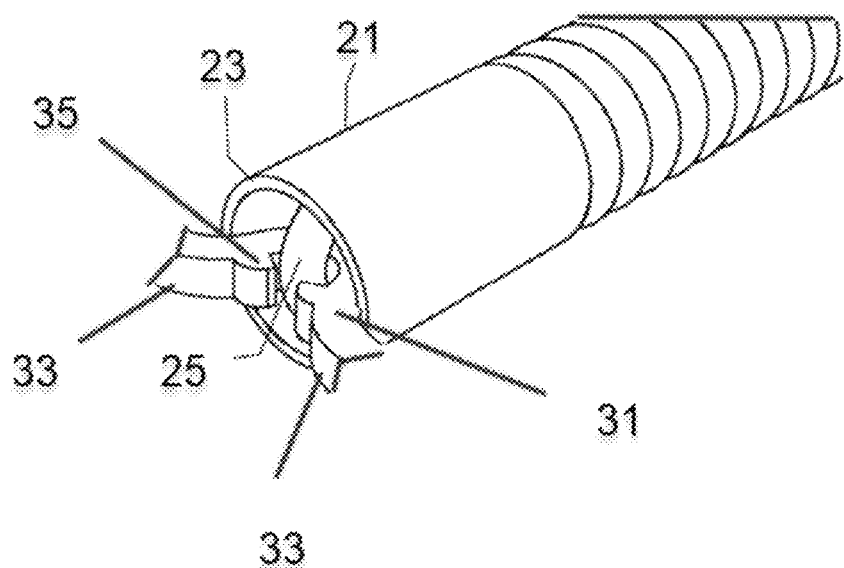
FIG. 1 is a fragmentary perspective view showing the present surgical staple attached to an endoscope adapter.
Figure 2:
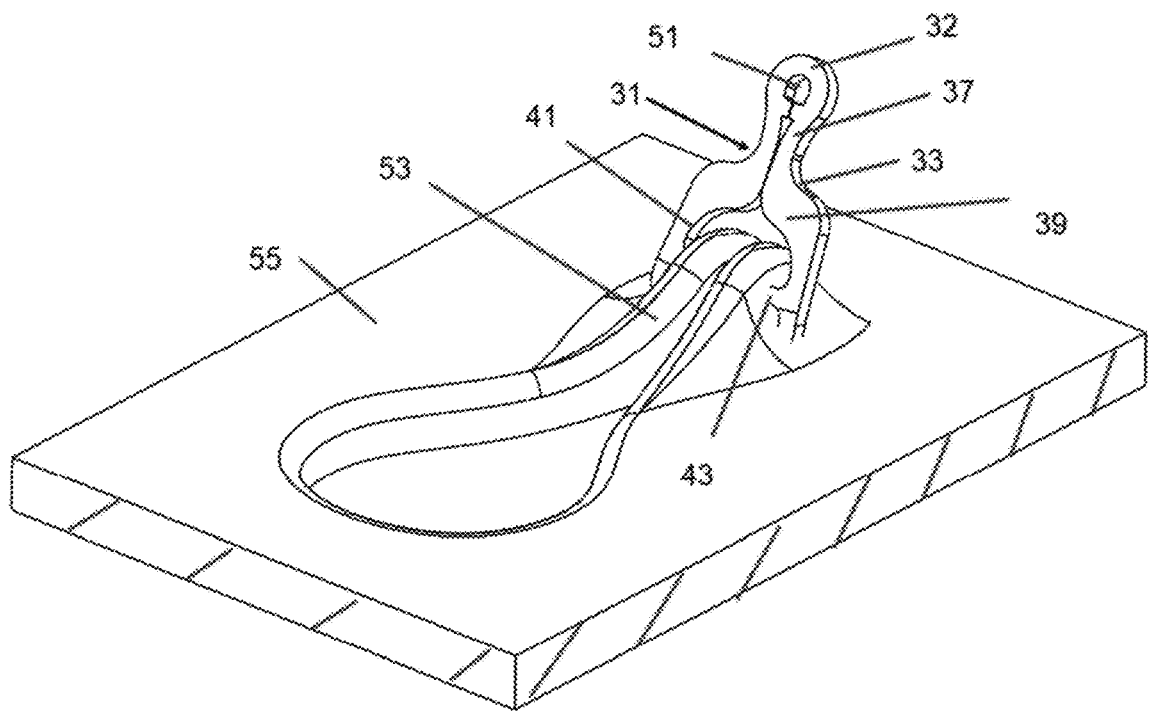
FIG. 2 is a fragmentary perspective view showing a first embodiment of the present surgical staple folded into a gripping position, stapling a patient's tissue.
Figure 4:
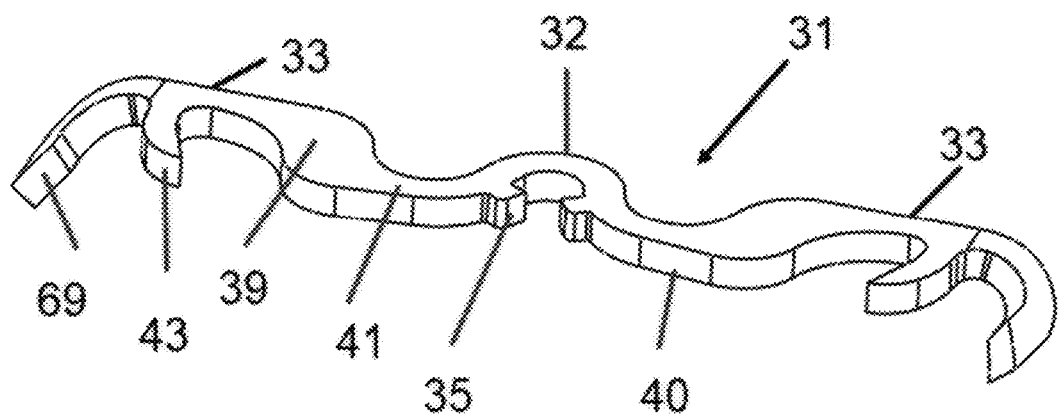
FIG. 4 is a perspective view showing the first embodiment of the present surgical staple.

The different embodiments of the present surgical staple will now be discussed in greater detail hereinafter. FIGS. 1 and 2 show a surgical staple 31 attached to an endoscopic applier tool 21. Applier tool 21 includes a surrounding and elongated cylindrical sleeve 23 and a centrally located hook 25. When applier tool 21 is internal to a patient and in the desired stapling location, hook 25 is retracted within sleeve 23. This causes hook 25 to pull on C-shaped transverse connection area 32, such that a distal edge of the sleeve serves as an anvil and deformably folds arms 33 of staple 31 toward each other. Accordingly, teeth 43 projecting from each arm 33 contacts against and firmly compresses flaps 53 of a patient's tissue 55, such as skin or an organ, to thereby staple the flaps together. Hook 25 is thereafter removed from a central gap 51 remaining in a transverse connection area 32 of the folded staple, such that gap 51 creates an eyelet shape. Preferably, the staple has a constant thickness and is cut from a single sheet of metal, such as titanium A first exemplary embodiment of the present surgical staple 31 is shown in greater detail in FIGS. 3 and 4. More specifically, bumpers or stops 35 are provided on a forward side edge of a foldable section 37 of transverse connection area 32, which abut against each other when in the folded position. Furthermore, each arm 33 includes a deformation area 41, having an arcuately curved backside edge and a generally flat surface 40 on an opposite forward side edge. A laterally enlarged resistance area 39 is disposed on each arm outboard of deformation area 41. A lateral width A of resistance area 39 is greater than lateral widths B and C of deformation area 41 and connection area 32, respectively. Preferably, width A is at least twice the distance of widths B and C. Moreover, width A is greater than, and preferably at least twice a lateral width D of the arm adjacent laterally projecting grippers or teeth 43 and 69. Opposite forward and back edges at resistance area 39, at width A, are generally parallel to each other. A back side edge surface 38 of each arm, between resistance area 39 and an arcuate transition to outboard tooth 69, is generally flat.

The forward and back edges of transition 32 are arcuately curved and back edge of deformation areas 41 are reverse arcuately curved, thereby creating a generally W-shape. A generally flat surface 40 is disposed on the forward edge of resistance area 39 which outwardly transitions into a curve defining a concave recess 61 where a hook-shaped inner tooth 43 laterally projects therefrom. Inner tooth 43 has a pointed distal end 65 offset to an inboard side thereof. Another curved recess 67 is between inner tooth 43 and an outer hook-shaped tooth 69 laterally and downwardly projecting therefrom. Outer tooth 69 includes a pointed distal end 71 offset toward its outboard edge, and a declining taper 73 extending from pointed end 71 toward recess 67. Flat surface 38 is on the back edge spanning across recesses 61 and 67 on an opposite side thereof.

Flat surfaces 40 and the laterally enlarged widths of resistance areas 39 abut and contact against each other when staple 31 is in its folded and stapling condition as illustrated in FIG. 2. These features advantageously deter overclosure and accurately control where the staple will deform (i.e., at the thinner width areas such as at B and C) during folding. The hook-like shape of teeth 43 and 69 pull on and firmly anchor tissue flaps 53 together.

Figure 5:
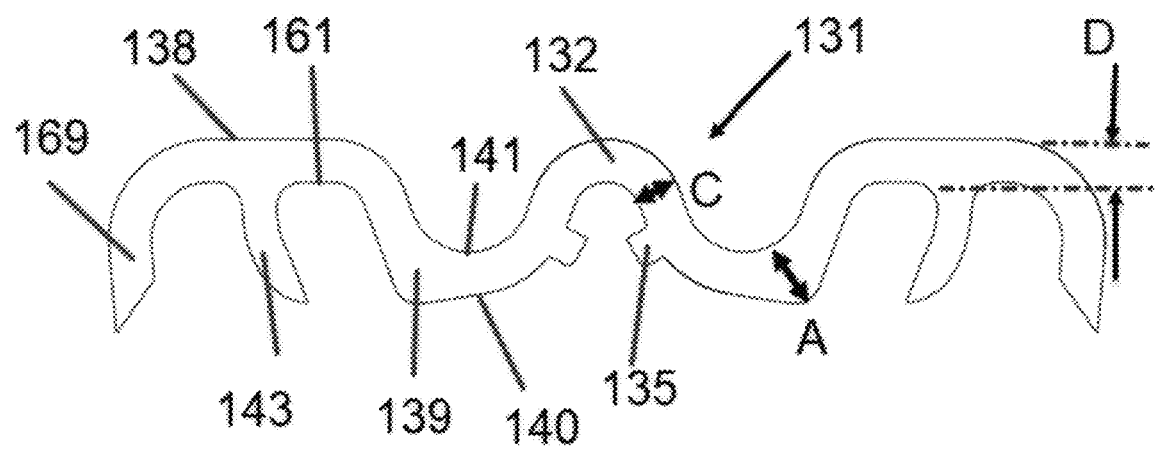
FIG. 5 is an elevational view showing a second embodiment of the present surgical staple.
Figure 6:
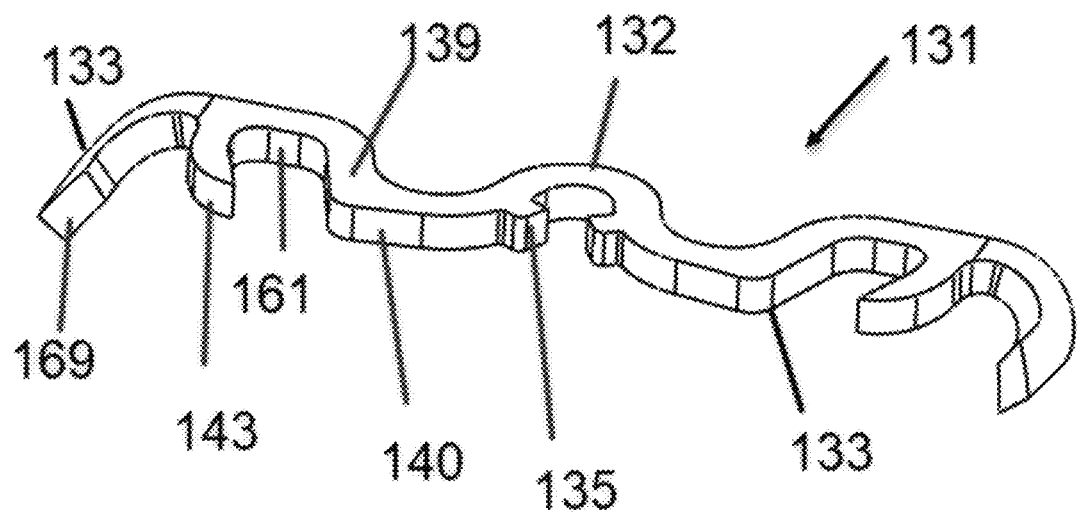
FIG. 6 is a perspective view showing the second embodiment of the present surgical staple.

A second embodiment of the present surgical staple 131 can be observed in FIGS. 5 and 6. Bumpers or stops 135 are provided on a forward side edge of transverse connection area 132, which abut against each other when in the folded position. Furthermore, each arm 133 includes a deformation area 141, having an arcuately curved backside edge and a generally flat surface 140 on an opposite forward side edge. A laterally enlarged resistance area 139 is disposed on each arm outboard of deformation area 141 and at the outboard segment of flat surface 140. A lateral width A of resistance area 139 is greater than lateral width C of the inboard segment of deformation area 141 and connection area 132. Thinner width C is generally constant on both sides of stop 135. Resistance area 139 with width A is at the transition from transition area 141 and flat 140, to the laterally extending section of a recess 161. Moreover, width A is greater than a lateral width D of the arm adjacent laterally projecting gripping teeth 143 and 169. A back side edge surface 138 of each arm, between resistance area 139 and an arcuate transition to outboard tooth 169, is generally flat.

The forward and back edges of transition 132 are arcuately curved and back edge of deformation areas 141 are reverse arcuately curved, thereby creating a generally W-shape. Generally flat surface 140 is disposed on the forward edge of resistance area 139 which outwardly transitions into a curve defining concave recess 161 where a hook-shaped inner tooth 143 laterally projects therefrom. Inner tooth 143 has a pointed distal end offset to an inboard side thereof. Another curved recess is between inner tooth 143 and an outer hook-shaped tooth 169 laterally and downwardly projecting therefrom. Outer tooth 169 includes a pointed distal end offset toward its outboard edge, and a declining taper extending from its pointed end toward its adjacent recess. Flat surface 138 is on the back edge spanning across the recesses on an opposite side thereof.

Flat surfaces 140 and the laterally enlarged widths of resistance areas 139 abut and contact against each other when staple 131 is in its folded and stapling condition as illustrated in FIG. 2. These features advantageously deter overclosure and accurately control where the staple will deform (i.e., at the thinner width areas such as at C) during folding. The hook-like shape of teeth 143 and 169 pull on and firmly anchor tissue flaps 53 together.

Figure 7:
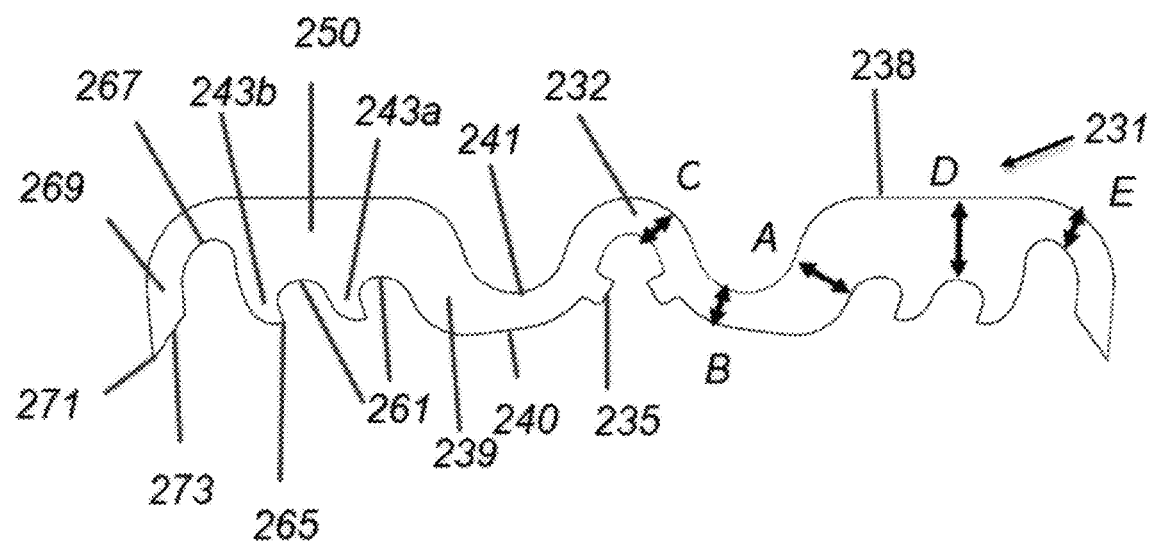
FIG. 7 is an elevational view showing a third embodiment of the present surgical staple.
Figure 8:
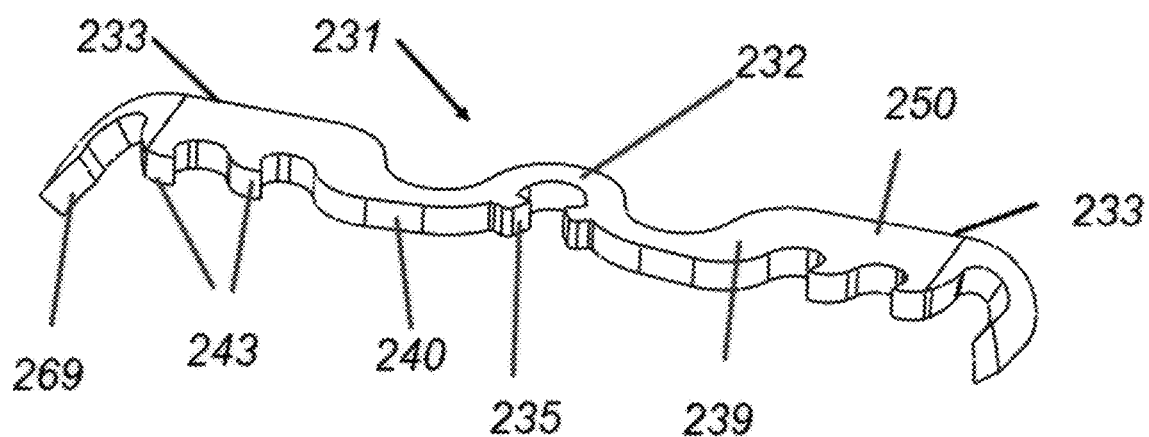
FIG. 8 is a perspective view showing the third embodiment of the present surgical staple.

FIGS. 7 and 8 show a third exemplary embodiment of the present surgical staple 231, which has a hemostasis clip configuration. Bumpers or stops 235 are provided on a forward side edge of transverse connection area 232, which abut against each other when in the folded position. Furthermore, each arm 233 includes a deformation area 241, having an arcuately curved backside edge and a generally flat surface 240 on an opposite forward side edge. A laterally enlarged resistance area 239 is disposed on each arm outboard of deformation area 241 and at the outboard segment of flat surface 240. A width A of resistance area 239 is greater than lateral widths B and C of connection area 232 and the inboard segment of deformation area 241, respectively. Thinner widths B and C are generally constant on both sides of stop 235. Resistance area 239 with width A is at the transition from transition area 241 and flat 140, to the laterally extending section of an inboard one of recesses 261. Moreover, lateral width D between flat and longitudinally extending back side 238 and recesses 261, is greater than a widths E, at outboard recess 267, and A.

This configuration includes three laterally projecting gripping teeth 243a, 243b and 269. Inboard and middle recesses 261 are shallower than is outboard recess 267. Thus, an outboard resistance area 250 is also provided on each arm 233, between inboard resistance area 239 and outboard tooth 269.

The forward and back edges of transition 232 are arcuately curved and back edge of deformation areas 241 are reverse arcuately curved, thereby creating a generally W-shape. Generally flat surface 240 is disposed on the forward edge of resistance area 239 which outwardly transitions into a curve defining concave recess 261 where a hook-shaped inner tooth 243a laterally projects therefrom. Inner teeth 243a and 243b each have a pointed distal end 265 offset to an inboard side thereof. Moreover, outer hook-shaped tooth 269 laterally and downwardly projects and includes a pointed distal end 271 offset toward its outboard edge, with a declining taper 273 extending from its pointed end toward its adjacent recess 267.

Flat surfaces 240 and the laterally enlarged widths of resistance areas 239 abut and contact against each other when staple 231 is in its folded and stapling condition as illustrated in FIG. 2. These features advantageously deter overclosure and accurately control where the staple will deform (i.e., at the thinner width areas such as at B and C) during folding. This hemostasis clip has blunt teeth which acts to anchor the staple on the GI wall and apply even compression force to the tissue.

Figure 9:
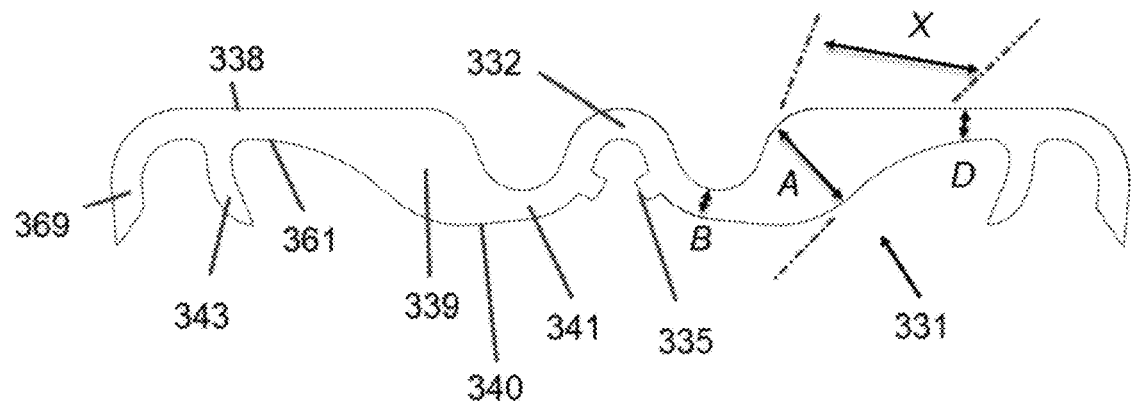
FIG. 9 is an elevational view showing a fourth embodiment of the present surgical staple.
Figure 10:
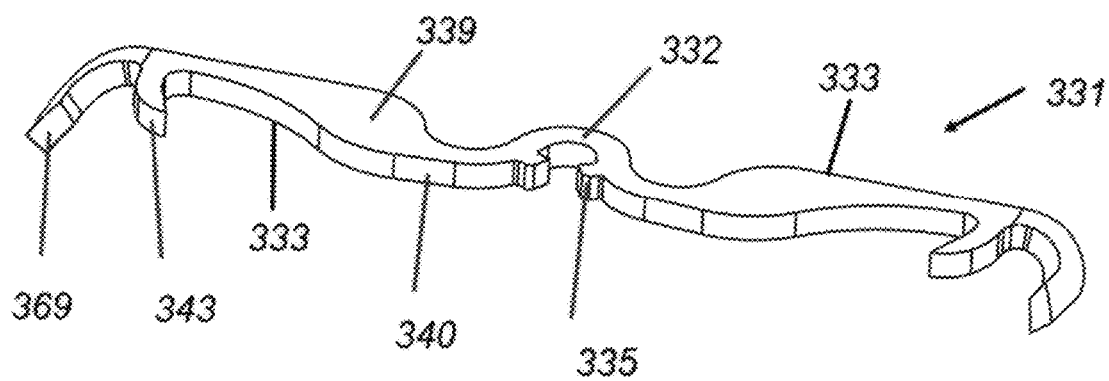
FIG. 10 is a perspective view showing the fourth embodiment of the present surgical staple.

A fourth embodiment of the present surgical staple 331 is presented in FIGS. 9 and 10. Bumpers or stops 335 are provided on a forward side edge of transverse connection area 332, which abut against each other when in the folded position. Furthermore, each arm 333 includes a deformation area 341, having an arcuately curved backside edge and a generally flat surface 340 on an opposite forward side edge. A laterally enlarged resistance area 339 is disposed on each arm outboard of deformation area 341. A width A of resistance area 339 is greater than lateral width B of deformation area 341 and connection area 332. Thinner width B is generally constant on both sides of stop 335. Resistance area 339 with width A is at the transition from transition area 341 and flat 340, to the diagonally extending section and smoother forward edge of a recess 361. Forward edge of resistance area 339 and recess 361 have a larger radius than in the other embodiments discussed hereinabove, with a more gradual transition until the surface is adjacent inner tooth 343.

Moreover, width A is greater than a lateral width D of the arm adjacent laterally projecting gripping tooth 343. There is an offset angle X between forward and back edges at resistance area 339, with the back edge being steeper and more lateral than the forward edge. A back side edge surface 338 of each arm, from resistance area 339 and an arcuate transition to outboard tooth 369, is generally flat and longitudinally straight.

The forward and back edges of transition 332 are arcuately curved and back edge of deformation areas 341 are reverse arcuately curved, thereby creating a generally W-shape. Generally flat surface 340 is disposed on the forward edge of resistance area 339 which outwardly transitions into a curve defining concave recess 361 where a hook-shaped inner tooth 343 laterally projects therefrom. Another curved recess is between inner tooth 343 and an outer hook-shaped tooth 369 laterally and downwardly projecting therefrom.

Flat surfaces 340 and the laterally enlarged widths of resistance areas 339 abut and contact against each other when staple 331 is in its folded and stapling condition as illustrated in FIG. 2. These features advantageously deter overclosure and accurately control where the staple will deform (i.e., at the thinner width areas such as at B) during folding. The hook-like shape of teeth 343 and 369 pull on and firmly anchor tissue flaps 53 together.

Figure 11:
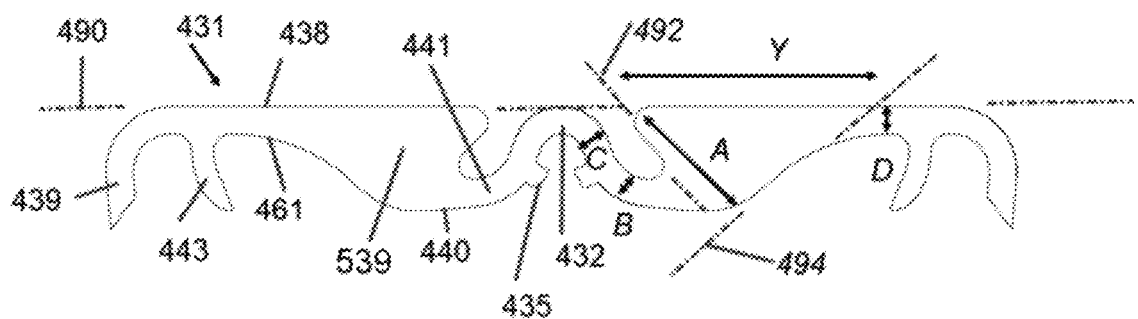
FIG. 11 is an elevational view showing a fifth embodiment of the present surgical staple.
Figure 12:
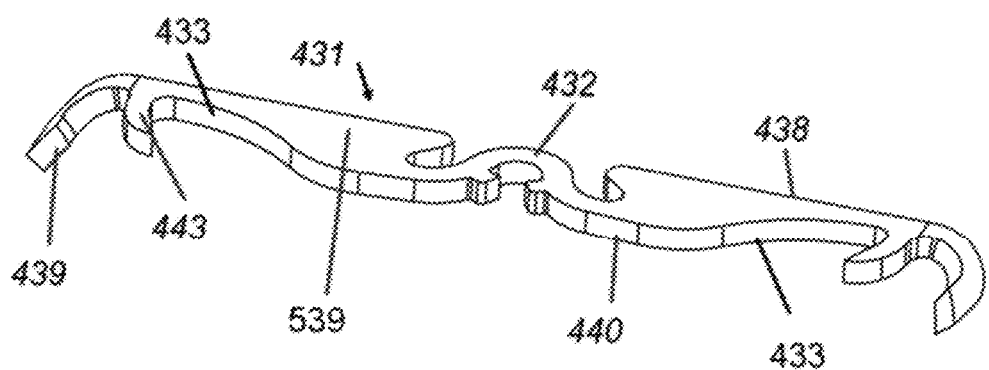
FIG. 12 is a perspective view showing the fifth embodiment of the present surgical staple.

Finally, reference should now be made to FIGS. 11 and 12. A fifth embodiment of the present surgical staple 431 includes bumpers or stops 435 on a forward side edge of transverse connection area 432, which abut against each other when in the folded position. Furthermore, each arm 433 includes a deformation area 441, having an arcuately curved backside edge and a generally flat surface 440 on an opposite forward side edge. A laterally and longitudinally enlarged resistance area 539 is disposed on each arm outboard of deformation area 441. A width A of resistance area 539 is greater than lateral width B of deformation area 441 and a lateral width C of connection area 432. Additionally, resistance area 439 has a back edge corner or nose with an internal surface 492 somewhat pointing toward a centerline and also toward longitudinal line 490. Therefore, a narrow, continuously curving and somewhat teardrop-shaped recess is formed in backside between connecting area 432 and restricted area 539.

Resistance area 539 of width A is at the transition from transition area 441 and flat 440, to the diagonally extending section and smoother forward edge of a recess 461. Forward edge of resistance area 539 and recess 461 have a larger radius than in the other embodiments discussed hereinabove, with a gradual transition until the surface is adjacent inner tooth 443.

Moreover, width A is greater than a lateral width D of the arm adjacent laterally projecting gripping tooth 443. Width A is at least twice and more preferably, at least four times greater than widths B, C and D. There is an offset angle Y between a line 494 at forward edge and a line 492 at back edge of resistance area 539, of approximately 90°+/−10°, both lines being angularly offset and not perpendicular to line 490. A back side edge surface 438 of each arm, from the nose to an arcuate transition of outboard tooth 439, is generally flat and longitudinally straight (coinciding with line 490).

The forward and back edges of transition 432 are arcuately curved and back edge of deformation areas 441 are reverse arcuately curved. Generally flat surface 440 is disposed on the forward edge of resistance area 539 which outwardly transitions into a curve defining concave recess 461 where a hook-shaped inner tooth 443 laterally projects therefrom. Another curved recess is between inner tooth 443 and an outer hook-shaped tooth 469 laterally and downwardly projecting therefrom.

Flat surfaces 440 and the laterally enlarged widths of resistance areas 539 abut and contact against each other when staple 431 is in its folded and stapling condition as illustrated in FIG. 2. These features advantageously deter overclosure and accurately control where the staple will deform (i.e., at the thinner width areas such as at B) during folding. The present exemplary configuration resists back-bending. The hook-like shape of teeth 443 and 469 pull on and firmly anchor tissue flaps 53 together.

Flat surfaces 440 and the laterally enlarged widths of resistance areas 439 abut and contact against each other when staple 431 is in its folded and stapling condition as illustrated in FIG. 2. These features advantageously deter overclosure and accurately control where the staple will deform (i.e., at the thinner width areas such as at B) during folding. The present exemplary configuration resists back-bending. The hook-like shape of teeth 443 and 469 pull on and firmly anchor tissue flaps 53 together.

While various configurations have been disclosed hereinabove, additional variations may be employed with the present surgical staple. For example, a greater or lesser quantity of teeth, and teeth of different shapes, may be used with the present staple, although certain advantages may not be realized. Furthermore, different longitudinal and lateral dimensions may be provided for some or all of the areas and sections of the staple, although some benefits may not be achieved. Alternate materials may be used, but some features may not be obtained. Structural and functional features of each embodiment may be interchanged between other embodiments disclosed herein. It is intended by the following claims to cover these and any other departures from the disclosed embodiments which fall within the true spirit and scope of the present invention.

The invention claimed is:

1. A surgical staple comprising:
two arms emerging from a transverse connection area;
each of the arms comprising a gripping area and a resistance area, the resistance area having an increased width located between the connection area and the gripping area;
the gripping area of each of the arms including at least two forwardly projected teeth;
a stop forwardly projecting from the connection area on each of the arms, each of the stops being configured to abut against each other when the staple is folded;
a flat surface located on a forward edge between the stop and the resistance area on each of the arms.

2. The surgical staple of claim 1, wherein the resistance area of each of the arms has a maximum width that is at least double a width of the connection area, and a width of the engaging area between the resistance area and the innermost of the teeth, is less than the maximum width of the resistance area.

3. The surgical staple of claim 1, wherein the resistance area of each of the arms has a width that is at least double a width of a deformation area located between the connection area and the resistance area, and a backside edge at the resistance area is parallel to or more steeply angled than the forward edge on an opposite side of the resistance area.

4. The surgical staple of claim 1, wherein the flat surfaces are configured so that when the staple is folded, the flat surfaces contact each other.

5. The surgical staple of claim 4, wherein:
the resistance area spans in a substantially diagonal direction between the flat surface and a section of each of the arms from which the teeth project;
a tissue-facing edge of the resistance area is part of a recess bordering an inner tooth of the the teeth;
the inner tooth including a pointed distal end;
an outermost tooth of the teeth including a pointed distal end and an adjacent taper which faces the inner tooth; and
the staple is configured for folding by an applier.

6. A surgical staple comprising an arcuate and central connecting area, and arms longitudinally extending from the connecting area, each of the arms comprising:
an arcuate deformation area extending from the connecting area, at least one of the connecting area and the deformation area being foldable;
a resistance area extending laterally outboard of the deformation area, the resistance area having a resistance width greater than: a connecting width of the connecting area, and a deformation width of the deformation area;
a backside edge at the resistance area is parallel to or more steeply angled than a tissue-facing edge on an opposite side of the resistance area;
multiple teeth laterally projecting from the tissue-facing edge of each of the arms; and
a width of a recess between the resistance area and an innermost of the teeth, is less than the resistance width.

7. The surgical staple of claim 6, further comprising:
a stop projecting from the tissue-facing edge of the connecting area; and
the resistance area including a flat surface on the tissue-facing edge thereof, with an arcuate portion of the deformation area being located between the stop and the flat surface, the flat surface being located between the stop and the innermost of the teeth.

8. The surgical staple of claim 6, further comprising:
a stop projecting from tissue-facing edge of the connecting area;
the resistance area including a flat surface on the tissue-facing edge thereof;
the connecting area being configured to engage a movable endoscopic hook; and
the arms being foldable toward each other such that the stops of the arms and the flat surfaces of the arms abut each other when folded.

9. The surgical staple of claim 6, wherein:
the resistance area spans in a substantially diagonal direction between a flat surface and a section of each of the arms from which the teeth project;
the tissue-facing edge of the resistance area is part of the recess bordering the innermost tooth of a gripping area;
the innermost tooth including a pointed distal end;
an outermost tooth of the teeth including a pointed distal end and an adjacent taper which faces the innermost tooth; and
the staple is configured for folding by an applier.

10. The surgical staple of claim 6, wherein the resistance area has the tissue-facing edge and the backside edge, the edges being substantially parallel to each other at a widest dimension of the resistance area as measured perpendicular to the backside edge thereof.

11. The surgical staple of claim 6, wherein the resistance area has a greatest width at a transition from a flat surface and the recess adjacent to the innermost of the teeth.

12. The surgical staple of claim 6, wherein the resistance area comprises an enlarged and protruding nose on the backside edge and adjacent a greatest width, which substantially points toward a centerline of the connecting area and toward the backside edge of an associated one of the arms, the nose substantially points away from the teeth on the associated one of the arms, and a narrow recess located between the connecting area and the nose which is open to the backside edge.

13. The surgical staple of claim 6, further comprising a segment of each of the arms having the teeth projecting from the tissue-facing edge thereof, the recess is part of arcuate recesses located between the teeth on the tissue-facing edge, and a width of the segment is less than a greatest dimension of the width of the resistance area as measured perpendicular to the tissue-facing edge.

14. The surgical staple of claim 6, wherein the backside edge of the resistance area is steeper than the opposite front tissue-facing edge of the resistance area, outboard of a flat surface on the tissue-facing edge outboard of the deformation area.

15. The surgical staple of claim 6, wherein the teeth include three teeth spaced apart by continually curved recesses including the recess between the innermost tooth and the resistance area, and an outboard recess is deeper with a concave base closer to the backside edge than the recesses on either side of the innermost of the teeth.

16. A surgical staple comprising a connector and arms extending from the connector, each of the arms comprising:
   a deformable section adjacent to the connector;
   an enlarged section coupled to the deformable section, a resistance area having a width greater than that of the connector and the deformable section;
   pointed teeth forwardly projecting from an outboard section;
   a stop forwardly projecting from the connector;
   a flat surface forwardly located on an enlarged area, the flat surface being located between the stop and the teeth;
   the connector being configured to engage a movable endoscopic puller; and
   the arms being foldable toward each other such that the stops and the flat surfaces of the enlarged sections abut each other when folded.

17. The surgical staple of claim 16, wherein the enlarged section has a greatest width at a transition from the flat surface and a recess adjacent to an innermost of the teeth, an outermost of the teeth includes a pointed distal end and an adjacent taper which faces an innermost of the teeth.

18. The surgical staple of claim 16, wherein the enlarged section comprises an enlarged nose adjacent a greatest portion of the width thereof, the nose substantially points away from the teeth on the associated one of the arms, and a substantially teardrop-shaped recess located between the connector and the nose which is open to and narrowest at a back edge.

19. The surgical staple of claim 16, wherein a back edge of the enlarged section is steeper than an opposite front edge of the enlarged section, outboard of the flat surface and outboard of the deformable section.

20. The surgical staple of claim 16, wherein the teeth include three teeth spaced apart by continually curved recesses, and an outboard recess is deeper with a concave base closer to a back edge than the inboard recesses on either side of innermost of the teeth.

\* \* \* \* \*